United States Patent [19]

DeVries et al.

[11] Patent Number: 5,127,400
[45] Date of Patent: Jul. 7, 1992

[54] VENTILATOR EXHALATION VALVE

[75] Inventors: Douglas F. DeVries, Redlands; Malcolm R. Williams, San Clemente; J. Kelly Dack, Riverside; Randy P. Hagen; Darrell W. Guillaume, both of Corona, all of Calif.

[73] Assignee: Bird Products Corp., Riverside, Calif.

[21] Appl. No.: 498,207

[22] Filed: Mar. 23, 1990

[51] Int. Cl.$^5$ .............................. A62B 9/02
[52] U.S. Cl. .................. 128/205.24; 128/204.23
[58] Field of Search ............... 128/204.18, 204.21, 128/204.23, 205.24

[56] References Cited

U.S. PATENT DOCUMENTS

| | | | |
|---|---|---|---|
| 4,524,804 | 6/1985 | Goedecke et al. | 137/625.64 |
| 4,535,816 | 8/1985 | Feder et al. | 137/625.65 |
| 4,540,018 | 9/1985 | Dantgraber | 137/540 |
| 4,548,382 | 10/1985 | Otting | 251/5 |
| 4,576,159 | 3/1986 | Hahn | 128/203.14 |
| 4,579,145 | 4/1986 | Leiber | 137/625.65 |
| 4,677,603 | 6/1987 | Kenjyo | 369/32 |
| 4,699,137 | 10/1987 | Schroeder | 128/205.24 |
| 4,821,767 | 4/1989 | Jackson | 137/491 |
| 4,838,257 | 6/1989 | Hatch | 128/204.18 |
| 4,840,457 | 6/1989 | Remer | 350/255 |

Primary Examiner—Edgar S. Burr
Assistant Examiner—Aaron J. Lewis
Attorney, Agent, or Firm—Knobbe, Martens, Olson & Bear

[57] ABSTRACT

A ventilator exhalation valve for controlling the exhalation flow rate and pressure is disclosed. The valve includes a free-floating diaphragm which is biased against a fixed valve seat in an inhalation configuration of the valve so as to prevent flow through the valve in the reverse direction. As flow in the forward direction passes through the valve, the bias urging the diaphragm onto the valve seat is overcome and the diaphragm is separated from the valve seat, so as to contact a poppet affixed to a shaft. The shaft includes a ferromagnetic portion and is attached to linear actuator which is retained by substantially frictionless suspension system including a pair of substantially planar spring flexures. As the poppet moves in response to flow between the fixed valve seat and the diaphragm, ferromagnetic portion of the shaft is displaced relative to a fixed coil thereby inducing a current in a coil. The current is monitored to provide a feedback signal corresponding to the velocity of the poppet. The feedback signal may be used by a control mechanism to increase the pressure stability of the valve.

6 Claims, 3 Drawing Sheets

VENTILATOR EXHALATION VALVE

BACKGROUND OF THE INVENTION

This invention relates to the field of medical ventilators, and more particularly, to a ventilator exhalation valve for regulating the expiration of respiratory gases from a patient to the atmosphere.

Medical ventilators provide artificial respiration to patients whose breathing ability is impaired. Typically, the ventilator employs an inhalation valve to deliver a breath to the patient from a pressurized source of gas and an exhalation valve for permitting the breath to pass from the lungs to the atmosphere. The flow of the breath during inspiration is governed by the inhalation flow-control valve. When the flow-control valve opens, the pressurized gas forming the breath is introduced into the lungs of the patient. Upon passage of a predetermined volume of gas, the flow-control valve closes to end the inspiration phase of the breath. After the inspiration phase, the respiratory gases are vented from the patient, through the exhalation valve to the atmosphere. The respiratory gases pass through the exhalation valve which provides flow control after inspiration is completed and before the next inspiration cycle begins.

Prior ventilators have been capable of operating in several modes so that the degree of support the ventilator provides to the natural breathing pattern of the patient can be varied over a broad spectrum. At one end of the spectrum, the ventilator can provide fully controlled ventilation in which the ventilator has complete control over when the breath is delivered, the volume of gases delivered to the patient during each breath and the timing and pressure of the respiratory gases. In the "volume controlled" mode, all of the flow parameters are preset by an operator in accordance with the particular needs of the patient.

At the other end, the ventilator can be programmed to permit "spontaneous" breathing by the patient. During the spontaneous breathing mode, the breath rate, the volume of gas inhaled during each breath and other flow parameters are not predetermined, but rather reflect the actual usage of the patient.

Intermediate of the volume controlled and the spontaneous modes, various degrees of ventilator supported respiration are available. One of the parameters which can be controlled by the ventilator during all modes of ventilation is the pressure in the lungs after the expiration phase is complete. Therapists have found that in some patients, it is beneficial to maintain a slight positive pressure within the lungs after expiration, so as to avoid a possible collapse of lungs. The pressure of the gases in or near the lungs and airway is called the "proximal pressure." Previous ventilators have included a "positive end expiration pressure" (PEEP) feature which enables the operator to determine and regulate the minimum proximal pressure after each expiration cycle is completed.

Previous ventilators have included micro-computer controllers which "servo" the position of the exhalation valve so as to regulate the proximal pressure to the desired level during the expiration phase of each breath, that is, the controller positions the valve based on feedback from a pressure sensor, and causes the movement of the valve as needed to maintain the desired proximal pressure. This is commonly referred to as a closed loop or "servo" control system.

Typical exhalation valves in closed loop ventilators generally fall into one of two configurations. The first configuration is the pneumatic balloon valve. In the pneumatic balloon valve a flexible balloon valve or diaphragm selectively engages a rigid seat in response to an externally generated pilot pressure. The pilot pressure is adjusted as required to close the valve during inspiration and open the valve during expiration so as to achieve the desired proximal pressure.

However, the pneumatic balloon valve is subject to the disadvantage that flow turbulence across the seat area generates a substantial audible noise in the form of "honk" or "squeal." In addition, the inherent delays in the transmission of the pneumatic pilot signal render the systems sluggish and difficult to control in a closed loop system. Further, the pilot pressure system required to drive the exhalation valve is a sensitive, mechanically complex and therefore expensive system.

The second configuration employed in exhalation valves is the electromechanical linear actuator. In the typical exhalation valve employing the linear actuator, the linear actuator takes the place of the pilot pressure. The linear actuator controls the valve by regulating the motion of a diaphragm relative to a valve seat. The linear actuator can be driven by electronics in a closed loop system to perform the various tasks of a ventilator including regulation of the proximal pressure.

However, the electromechanical linear actuator closed loop systems are subject to the disadvantage that the actuator slides in a bearing which experiences static and dynamic friction. The dynamic sliding friction creates discontinuities in the motion thereby making the system difficult to control. In addition, steady state error and instabilities may be generated as result of the friction. Further, due to a lack of positional or velocity feedback of the actuator, the system tends to an unstable configuration.

Therefore, a need exists for a ventilator exhalation valve for which may be used in a closed loop system without generating audible noise resulting from flow turbulence. A need also exists for a ventilator exhalation valve which provides for a dampening of turbulence in the flow. In addition, the need exists for a exhalation valve in a closed loop system which is readily responsive to control signals. A further need exists for an exhalation valve which does not require mechanically complex, expensive mechanisms to provide for the regulation of the proximal pressure. A further need exists for a ventilator exhalation valve which exhibits reduced instabilities so that a feedback system may be employed in a stable configuration.

SUMMARY OF THE INVENTION

The disclosed ventilator exhalation valve provides an exhalation valve which may be employed in a closed loop system without generating excessive noise due to fluid flow through the valve. The exhalation valve employs a linear actuator retained by a substantially frictionless suspension system thereby reducing discontinuities in control signals and providing an increased stability and responsiveness of the system. The exhalation valve also includes a free floating diaphragm which may move independently of the linear actuator, and thereby provide a check valve function in the exhalation valve. The disclosed valve includes a passive velocity coil which provides a velocity feedback signal which may be used to control the patient circuit pressure in a closed loop system. The velocity coil also dampens the inherent flow turbulence through the valve, thereby increasing the stability of the valve.

The disclosed ventilator exhalation valve employs an electromechanical linear actuator assembly controlled by an external control mechanism. The actuator assembly, in turn, controls a poppet which selectively engages a diaphragm to control the flow area through the valve. The actuator assembly is retained by a suspension assembly within a housing. The suspension assembly includes two flat spring flexures which provide a frictionless suspension of the actuator-driven poppet, eliminating the problems normally inherent with the use of friction bearings. The flexures are designed to provide maximum flexibility and continuity of motion in the axial direction, while maintaining maximum rigidity in the radial direction. The suspension system thereby provides for substantially frictionless and continuous axial motion of the poppet.

The diaphragm cooperates with a valve seat to create the variable flow area during the expiration of the respiratory gases. Preferably, the diaphragm is configured so that it can be selectively contacted by the poppet. As the diaphragm is not directly coupled to the poppet, the diaphragm may "float" when the poppet is retracted by the actuator assembly. That is, the diaphragm and poppet are capable of independent movement relative to the valve seat. Preferably, the diaphragm is nominally biased against the valve seat when there is no flow from the patient so as to provide an inherent check valve function, preventing reverse fluid flow through the exhalation valve during the inhalation phase. This provides an integral check valve function which prevents the patient from drawing gases through the exhalation valve in the reverse flow direction.

The velocity coil of the preferred embodiment includes a stationary coil electrically connected to the control mechanism and a ferromagnetic member which moves relative to the stationary coil corresponding to the motion of the poppet. That is, as the ferromagnetic member moves relative to the stationary coil, a signal having an amplitude and polarity approximately proportional to the speed and direction of the poppet is generated. The signal is used in the control mechanism to regulate the linear actuator and provide increased stability of the system.

Preferably, the exhalation valve also includes a valve body having an inlet port, an outlet port, the valve seat and a pressure sense port. The valve seat is disposed intermediate of the inlet port and the outlet port, and the pressure sense port is disposed between the valve seat and the inlet port. The pressure sense port thereby provides an integral passive pressure measuring point proximal to the valve so as to provide an accurate measurement of the patient pressure.

DETAILED DESCRIPTION OF THE DRAWINGS

DETAILED DESCRIPTION OF THE PREFERRED EMBODIMENT

Figure 1:
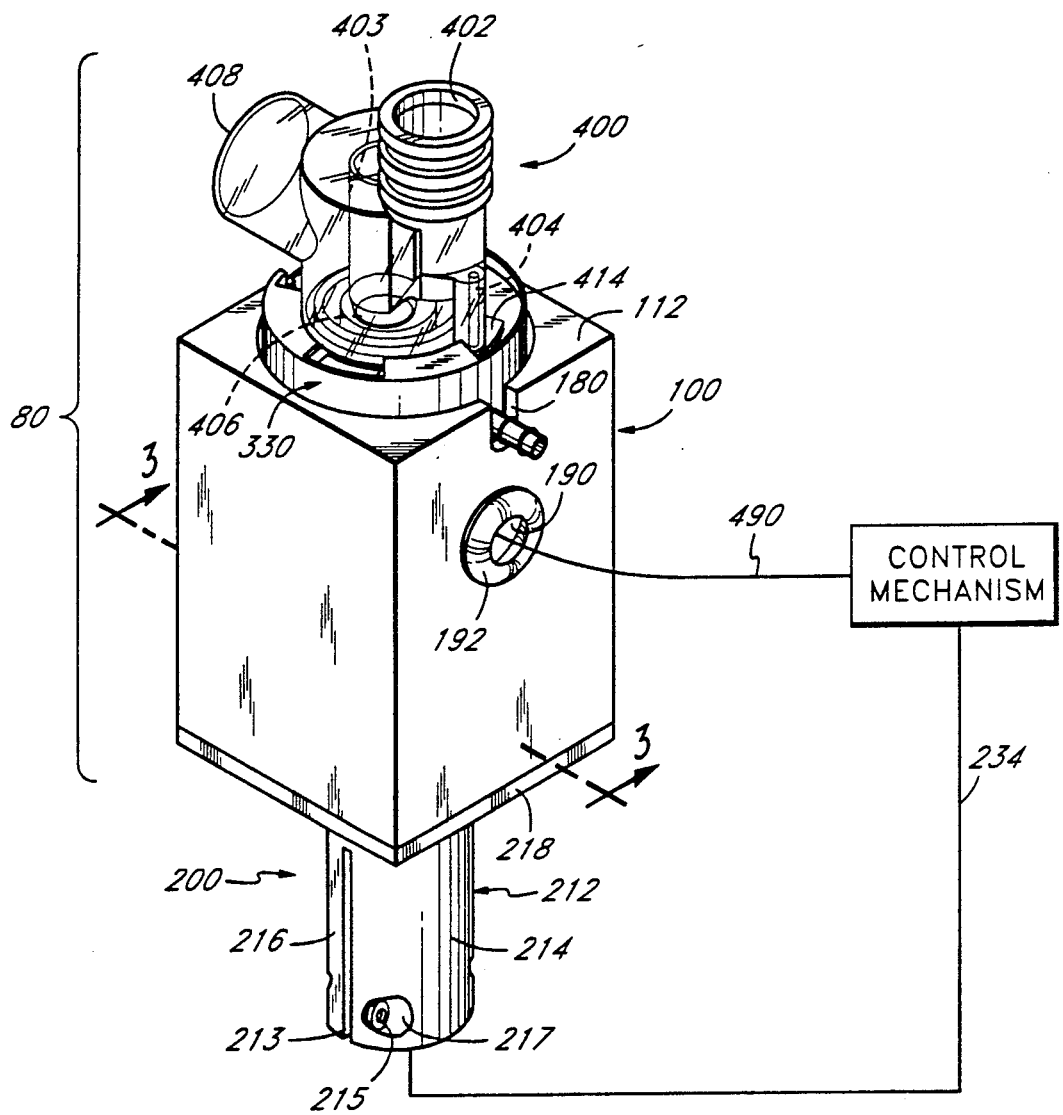
FIG. 1 is a perspective view of a ventilator exhalation valve.
Figure 3:
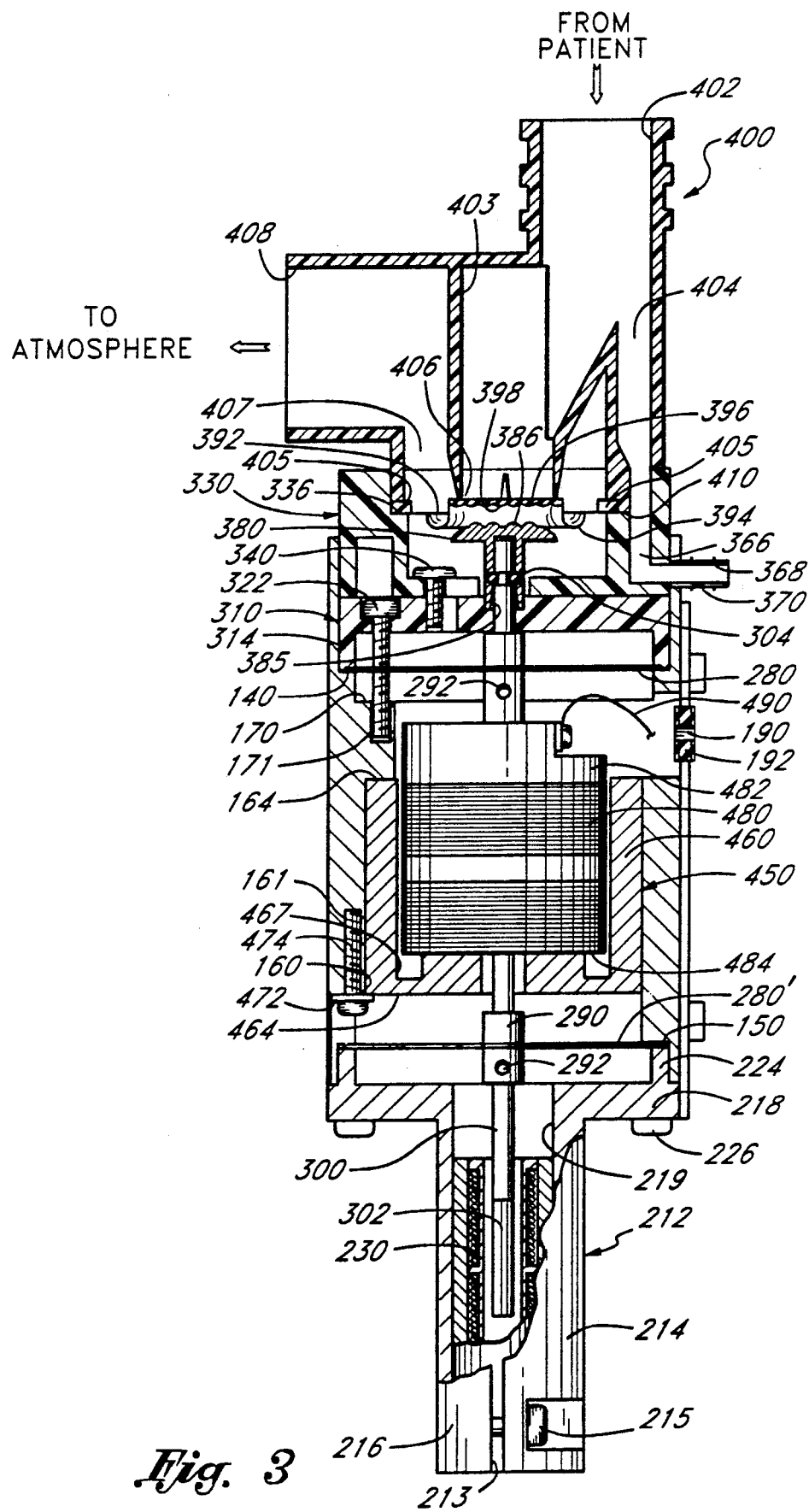
FIG. 3 is a partial cross-sectional view of the exhalation valve taken along lines 3—3 of FIG. 1.

Referring to FIGS. 1 and 3, the disclosed ventilator exhalation valve 10 includes a housing assembly 80, including a housing 100 and a valve body 400 operably connected to the housing 100 by an adaptor 330, and a feedback assembly 200.

Figure 2:
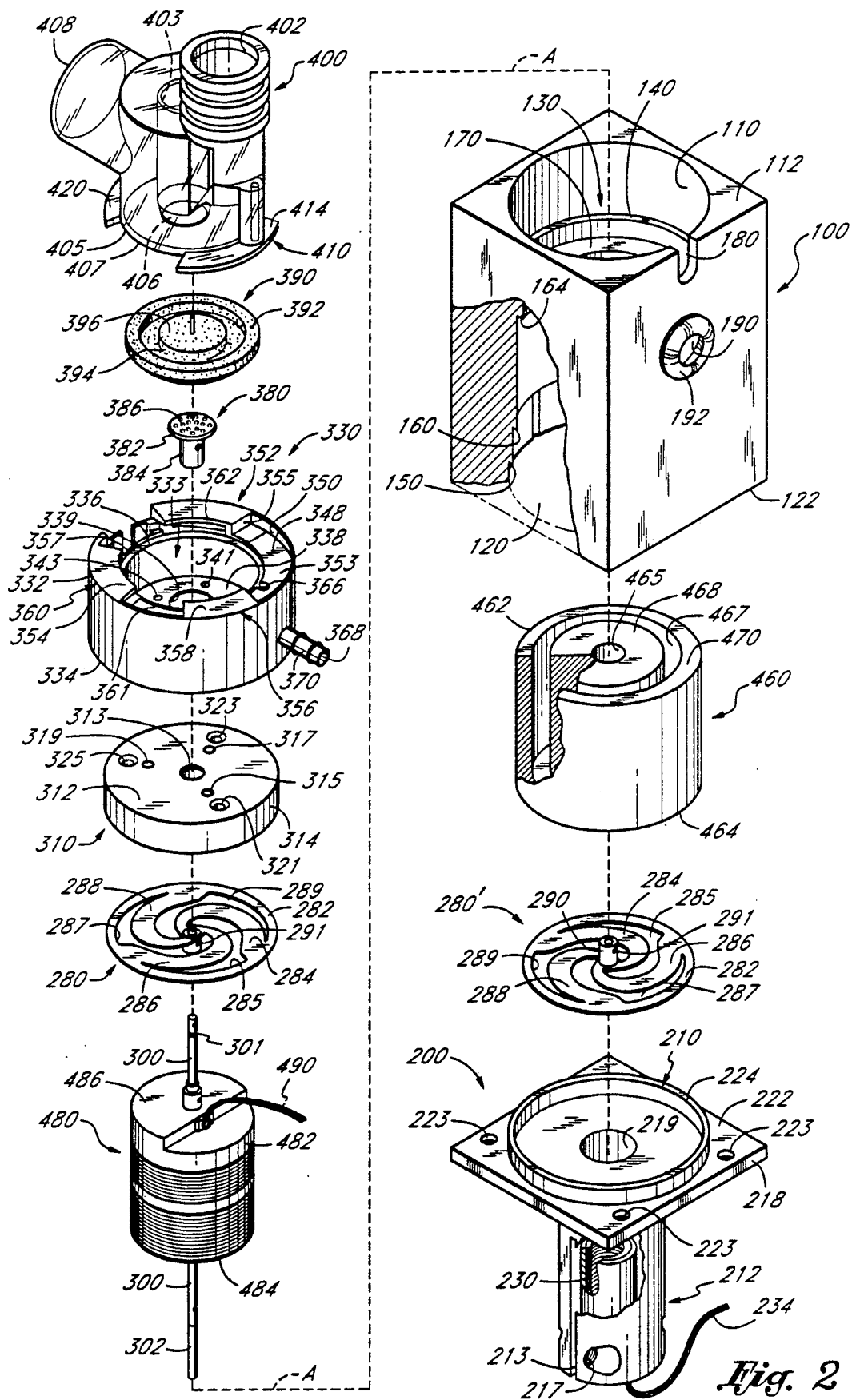
FIG. 2 is an exploded perspective of the components of the ventilator exhalation valve.

As shown in FIGS. 1, 2 and 3, the housing 100 is a substantially rectangular unit machined from an aluminum alloy such as 2024 T51. However, the housing 100 may take a variety of configurations and be formed of various materials, such as stainless steel or plastics. Referring to FIG. 2, the housing 100 includes a valving port 110 and a feedback port 120 coaxially aligned about an axis A which extends longitudinally through the housing 100. The valving port 110 and the feedback port 120 have a substantially circular periphery, and are defined by a common diameter. Referring to FIGS. 1 and 2, the valving port 110 terminates at a substantially planar valving surface 112, wherein the valving surface 112 is substantially perpendicular to the axis A. Referring to FIGS. 2 and 3, the feedback port 120 terminates at a substantially planar mating surface 122, such that the mating surface 122 is perpendicular to the axis A. The mating surface 122 includes a threaded recess (not shown) proximal to each corner of the housing 100.

A central cavity 130 connects the valving port 110 and the feedback port 120 through the housing 100. The cavity 130 has a substantially cylindrical configuration as it extends between the valving port 110 and the feedback port 120. The cavity 130 includes five circumferential shoulders which define the various diameters of the cavity. The shoulders include a first suspension shoulder 140, a second suspension shoulder 150, a mooring shoulder 160, an abutment shoulder 164 and a retainer shoulder 170.

The first suspension shoulder 140 is spaced from the valving port 110 and extends about the circumference of the cavity 130. The first suspension shoulder 140 is perpendicular to and concentric with the axis A, and faces the valving port 110. The first suspension shoulder 140 defines a smaller cavity diameter than the valving port 110.

The second suspension shoulder 150 is proximate to the feedback port 120 and extends about the circumference of the cavity 130. The second suspension shoulder 150 is perpendicular to and concentric with the axis A, and faces the feedback port 120. The second suspension shoulder 150 defines a smaller cavity diameter than the feedback port 120. Preferably, the first and second suspension shoulders 140, 150 are defined by a common diameter.

The mooring shoulder 160 is located between the first and second suspension shoulders 140, 150. Preferably, the mooring shoulder 160 is disposed proximal to the second suspension shoulder 150 so that the mooring shoulder 160 is nearer the feedback port 120 than the valving port 110. The mooring shoulder 160 is perpendicular to and concentric with the axis A, and faces the feedback port 120. The mooring shoulder 160 defines a smaller periphery then the second suspension shoulder 150. The mooring shoulder 160 includes three threaded recesses spaced approximately 120° from each other (only recess 161 is shown in FIG. 3). The recesses open at the shoulder 160 and extend into the housing 100.

The retainer shoulder 170 is disposed proximal to the first suspension shoulder 140. The retainer shoulder 170 is intermediate of the mooring shoulder 160 and the first suspension shoulder 140. The retainer shoulder 170 is perpendicular to and concentric with the axis A, and faces the valving port 110. The retainer shoulder 170 defines a smaller circumference than the first and second suspension shoulders 140, 150 and the mooring shoulder 160. The retainer shoulder 170 includes three threaded recesses spaced 120° from each other (only one recess 171 is shown in FIG. 3).

The abutment shoulder 164 is intermediate of the mooring shoulder 160 and the retainer shoulder 170. The abutment shoulder 164 is perpendicular to and concentric with the axis A, and faces the feedback port 120. The abutment shoulder 164 defines a smaller circumference than the mooring shoulder 160.

Referring to FIGS. 1 and 2, the housing 100 includes a notch 180 extending from the planar valving surface 112 towards the feedback port 120. The notch 180 exposes a length of the cavity 130 between the first suspension shoulder 140 and the valving surface 112 to the exterior of the housing 100.

As shown in FIGS. 1 and 2, the housing 100 includes an input port 190. The input port 190 exposes the cavity 130 to the exterior of the housing. As shown in FIG. 3, the input port 190 intersects the cavity 130 intermediate of the mooring shoulder 160 and retainer shoulder 170. A grommet 192 is retained in the input port 190 to provide a non-abrasive passage into the cavity 130.

Suspension Assembly

As shown in FIGS. 2 and 3, a suspension assembly 260 includes a pair of substantially planar spring flexures. Preferably, the spring flexures 280, 280' are made up of high strength stainless steel, preferably Sandvik 11 R51, manufactured by Sandvik of Svenska Försäljnings AB Sweden, having a thickness of approximately 0.002 inches. Preferably, the flexures 280, 280' are formed by chemically etching the desired configuration from a sheet of the material, as well known in the art. However, other methods such stamping or cutting may be employed. Referring to FIG. 2, each flexure includes a substantially solid circumferential periphery 282 concentrically oriented about an inner sleeve 290. Three spiral arms 284, 286, 288 connect the periphery 282 to the sleeve 290. The arms 284, 286, 288 extend from the periphery 282 at approximately 120° intervals in a radially inward direction. Each arm then spirals inward to connect to the sleeve 290 in a substantially radial intersection approximately 120° from connection of the arm to the periphery 282. The arms 284, 286, 288 taper in width from the periphery 282 to a narrower width at the sleeve 290. As shown in FIG. 2, this configuration provides three openings 285, 287, 289 proximal to the periphery 282 and spaced 120° from each other.

The flexures 280, 280' do not include the friction bearings previously used to accommodate the axial motion of the actuator assembly. Therefore, the flexures 280, 280' do not exhibit the discontinuances inherent in friction bearings. The flexures 280, 280' are configured to maximize axial flexibility so as to provide smooth continuous axial motion, while maximizing stiffness in the radial direction.

In a preferred embodiment, the outer diameter of the periphery 282 is approximately 1 13/16 inches and the width of the periphery 282 is approximately ⅛ inch. The periphery 282 is sized to contact the suspension shoulders 140, 150. At the intersection of an arm and the periphery 282, the arm has a width of approximately ⅜ of an inch. As the arm intersects the sleeve 290, the width of the arm is approximately ⅛ of an inch.

Preferably, the sleeve 290 is attached to the intersection of the arms 284, 286, 288 by sandwiching the flexure 280 between opposing parts of the sleeve 290. However, the sleeve 290 may be attached by other methods such as gluing, crimping, soldering or welding. In the preferred embodiment, the sleeve 290 has a longitudinal length of approximately ¼ inch and an inner diameter of approximately ⅛ inch. The sleeve 290 includes an aperture 291 extending substantially perpendicular to the sleeve; that is, radially from the longitudinal axis of the sleeve. A pin 292 may be received within the aperture to extend into the inner diameter of the sleeve 290.

Shaft

As shown in FIGS. 2 and 3, an elongate shaft 300 extends through the cavity 130 from the feedback assembly 200 to the valve body 400. The shaft 300 has a diameter of approximately ⅛ inch and may be formed of non-magnetic stainless steel. As shown in FIGS. 2 and 3, the shaft 300 is received within the sleeve 290 of each of the spring flexures 280, 280'. The pin 292 in the sleeve 290 is engaged with the shaft 300 so as to secure the shaft relative to the flexure. As the shaft 300 is secured to the flexures 280, 280', and the flexures are secured relative to the housing 100, as discussed infra, the flexures thereby permit substantially frictionless axial motion of the shaft; that is, longitudinal motion with respect to the axis A. As the periphery 282 is fixed with respect to the housing 100, when the shaft 300 moves in the axial direction, the sleeve 290 is axially displaced relative to the periphery of the flexure. Therefore, during axial motion of the shaft 300, the arms 284, 286, 288 flex axially, permitting the sleeve 290 to be axially displaced relative to the secured periphery 282.

In a preferred embodiment, the shaft 300, and hence sleeve 290, travel a total axial displacement of approximately 0.2 inches relative to the periphery 282 of the flexure. As there is no motion of the shaft relative to the sleeve, there is no friction during axial movement of the shaft 300. The resiliency of arms represent the resistance to the axial motion of the shaft.

Radial motion of the shaft 300 is substantially precluded by the spiral configuration of the arms so that bearings are not required to radially retain the shaft.

As shown in FIGS. 2 and 3, the shaft 300 includes a ferromagnetic portion 302 disposed proximal to the feedback assembly 200. The ferromagnetic portion 302 may be formed of ALNICO 8 and attached to the shaft 300 by an interference fit. Proximal to the opposing end of the shaft 300, the shaft includes an annular recess 301. The annular recess 301 is sized to partially receive an elastomeric O-ring 304.

Linear Actuator Assembly

Referring to FIGS. 2 and 3, a linear actuator assembly 450 is retained within the cavity 130. The linear actuator assembly 450 includes a permanent magnet 460, a moveable coil 480 and a flexible lead 490.

The permanent magnet 460 includes a housing which retains three ring magnets and carries the flux path. The three ring magnets are configured within the housing such that the permanent magnet 460 has a substantially cylindrical configuration defined by an open end 462 and a closed end 464. The circumference of the magnet 460 is sized to be slidably received within the periphery defined by the mooring shoulder 160. Preferably, the magnets are formed of Sumarium Cobalt. The permanent magnet 460 includes a longitudinal aperture 465 coincident with its central axis and the axis A. The magnet 460 also includes an annular recess 467 concentrically oriented with respect to the longitudinal aperture 465. The recess 467 extends from the open end 462 of the magnet, substantially the length of the magnet, to terminate proximal to the closed end 464. The recess 467 defines a peripheral inner face 468 and a peripheral outer face 470 of the open end 462 of the magnet.

Preferably, the length of cavity from the mooring shoulder 160 to the abutment shoulder 164 is substantially equal to the length of the magnet 460 such that the outer face 470 of the open end 462 of the magnet contacts the abutment shoulder 164, and the closed end 464 of the magnet is coplanar with the mooring shoulder 160. The cavity diameter defined by the abutment shoulder 164 is larger than the diameter of the recess 467 of the magnet 460, as the outer face 470 contacts the abutment shoulder. Therefore, the annular recess 467 of the magnet 460 is exposed to the cavity 130. As the permanent magnet 460 is received within the cavity 130, the magnet is secured to the housing 100 by washers 472 retained by a fastener 474, such as a bolt or screw, retained in the mooring shoulder 160. As seen in FIG. 3, the washers 472 have a sufficient diameter so as to extend beyond the mooring shoulder 160 to contact the closed end 464 of the magnet 460.

As shown in FIGS. 2 and 3, the moveable coil 480 has a cylindrical configuration sized to be received within the annular recess 467 of the permanent magnet 460. Preferably, the coil 480 is electrically conductive and wound around a cylindrical drum 482 which is affixed to the shaft 300 between the spring flexures 280, 280'. The drum 482 has an open end 484 and closed end 486, such that the open end 484 of the drum defines a circumference which is slidably received within the annular recess 467 of the permanent magnet 460. As shown in FIG. 3, the drum 482 is substantially disposed within the recess 467 of the magnet 460. As shown in FIG. 3, as the drum 482 is secured to the shaft 300, the open end 484 is spaced from the bottom of the recess 467 a sufficient distance so that upon the full axial travel of the drum relative to the magnet, the open end of the drum does not contact the magnet. The coil 480 is electrically connected to the flexible lead 490. The flexible lead 490 exits the housing 100 through the input port 194 and is connected to the external control mechanism. The flexible lead 490 allows for axial motion of the movable coil 480 relative to the housing 100 without creating a resistance to the axial motion of the coil. Preferably, the movable coil 480 is formed of copper wire and wound around the drum 482 such that a substantial portion of the coil 480 is disposed within the annular recess 467 of the permanent magnet 460.

Displacement of the movable coil 480 relative to the magnet 460 is accomplished by axial displacement of the shaft 300. When the shaft 300, as retained by the flexures 280, 280', moves axially, the drum 482 and coil 480 are thereby axially displaced relative to the permanent magnet 460.

Velocity Feedback Assembly

As shown in FIGS. 2 and 3, the velocity feedback assembly 200 is affixed to the housing 100 at the feedback port 120. The feedback assembly 200 includes a retainer 210, the ferromagnetic portion 302 of the shaft 300, a passive stationary coil 230 and a signal path 234.

Although the retainer 210 is preferably formed of machined aluminum, the retainer may be formed from a variety of other materials, such as stainless steel or plastics. In FIGS. 1-3, the retainer is shown as an independent structure, however, the retainer may be formed substantially integral with the housing 100. Referring to FIGS. 1-3, the retainer 210 includes a cylindrical clamp 212 affixed to a perpendicular support 218. A central aperture 219 extends through the support 218 and the clamp 212. Preferably, the aperture 219 is concentric with the cavity 130 and axis A.

The support 218 includes a substantially planar mating face 222. The mating face 222 is sized to match the mating surface 122 of the housing 100. Preferably, the mating face 222 also includes a plurality of apertures 223 which correspond to and align with threaded recesses in the mating surface 122 of the housing 100 so that the retainer 210 may be secured relative to the housing 100.

A circular ridge 224 extends from the mating face 222. The ridge 224 has a diameter equal to the diameter of the second suspension shoulder 150 and the periphery 282 of the spring flexure. The height of the ridge 224 is a substantially equal distance from the second suspension shoulder 150 to the mating surface 122 of the housing 100. The securing of the retainer 210 to the housing 100 provides for the retention of a flexure 280' on the second suspension shoulder 150. The ridge 224 is sized to engage the second suspension shoulder 150 so as to retain the periphery 282 of a flexure 280' therebetween.

The sleeve 290 of the flexure 280' is passed over the shaft 300 and the flexure is then secured to the shaft so that the periphery 282 of the flexure contacts the second suspension shoulder 150. As the retainer 210 is cooperatively aligned with the housing 100, the ridge 224 contacts the periphery 282 as it seats on the second suspension shoulder 150. The mating face 222 and the mating surface 122 then define a common plane and fasteners 226 may be passed through the apertures 223 and into the recesses to secure the retainer 210 and the flexure 280' relative to the housing 100.

Referring to FIGS. 1, 2 and 3, the clamp 212 includes opposing slits 213, 213' (not shown) which extend from proximal to the support 218 to the distal end of the clamp 212. The slits 213, 213' thereby form opposing halves 214, 216 of the clamp 212. At the distal end of the clamp 212, the opposing halves 214, 216 include aligned recesses 217 which accommodate a threaded fastener 215. The fasteners 215 draw the halves 214, 216 closer together, thereby selectively narrowing the slits 213, 213' and the aperture 219 within the clamp 212.

As shown in FIGS. 2 and 3, a stationary cylindrical coil 230 is disposed within the central aperture 219 of the clamp 212. Preferably, the stationary coil 230 is sized to slidably receive the ferromagnetic portion 302 of the shaft 300 without actually contacting the shaft. In addition, the stationary coil 230 has a sufficient length so that throughout the full range of axial travel of the ferromagnetic portion 302 relative to the coil, the ferromagnetic portion remains within the coil. The stationary coil 230 is electrically conductive and formed of copper wire having approximately 850 turns. The coil 230 is retained in the clamp 212 by selectively narrowing the slits 213, 213', thereby pinching the coil 230 within the clamp 212.

A signal path 234 extends from the stationary coil 230 to the control mechanism. The signal path 234 provides communication from the feedback assembly 200 to the control mechanism.

The velocity feedback assembly 200 provides a signal proportional to the velocity of the shaft 300. As the ferromagnetic portion 302 is disposed within the stationary coil 230, any axial motion of the shaft 300 causes the ferromagnetic portion 302 to be moved relative to the stationary coil 230. The movement of the ferromagnetic portion 302 within the stationary coil 230 generates a current in the stationary coil 230 having an amplitude and polarity approximately proportional to the velocity of the shaft 300 relative to the housing 100. The feedback signal passes through the signal path 234 to the control mechanism.

Valving Mechanism

The valving mechanism includes a valve body 400, an adaptor 330, a poppet 380 and a diaphragm 390.

As shown in FIGS. 2 and 3, a retainer 310 is disposed within the cavity 130 intermediate of the adaptor 330 and the housing 100. Although the disclosed valve 10 may be constructed without the retainer 310, the retainer provides for simplified manufacturing of the valving mechanism. Although the retainer 310 is formed of aluminum, the retainer may be formed of other metals such as stainless steel. The retainer 310 includes a substantially circular planar member 312 and a depending peripheral rim 314. The peripheral rim 314 has a circumference substantially equal to the first suspension shoulder 140. The planar member 312 of the retainer 310 includes a central aperture 313 sized to slidably receive the shaft 300. The planar member 312 also includes three inner apertures 315, 317, 319 spaced approximately 120° apart about a circumference proximal to the central aperture 313. The apertures 315, 317, 319 are threaded to engage a fastener 316 or alternatively, may be sized smaller than a fastener shank so as to provide a self-tapping type retention.

As shown in FIGS. 2 and 3, the planar member 312 also includes three outer apertures 321, 323, 325 spaced approximately 120° from each other about a circumference proximal to the peripheral rim 314. Preferably, the outer apertures 321, 323, 325 are within the circumference defined by the rim 314. Referring to FIG. 3, the outer apertures 321, 323, 325 align with the corresponding recesses of the retainer shoulder 170 and the openings 285, 287, 289 of the spring flexure 280.

The retainer 310 is secured within the cavity 130 so as to retain a flexure 280 relative to the housing 100. The periphery 282 of the flexure 280 is seated upon the first suspension shoulder 140 and the peripheral rim 314 of the retainer 310, then seats on the periphery 282 of the flexure 280 so that the flexure is retained between the peripheral rim 314 and the first suspension shoulder 140.

As the recesses of the retainer shoulder 170 are spaced approximately 120° from each other, and the openings 285, 287, 289 of the flexure 280 are approximately 120° from each other on a coincident circumference, the recesses and the openings cooperatively align. The outer apertures 321, 323, 325 of the retainer 310 align with the threaded recess of the retainer shoulder 170 for securing the retainer 310 relative to the housing 100. A fastener 322 is passed through the outer aperture 321, through an opening in the flexure 280, and into a recess in the retainer shoulder 170 to secure the retainer 310 relative to the housing 100. The retainer 310 may thereby be secured relative to the housing 100 while retaining the flexure 280 between the peripheral rim 314 and the first suspension shoulder 140.

The adaptor 330 is received within the cavity 130 so as to contact the planar member 312 of the retainer 210. The adaptor 330 has a coupling end 332 and a secured end 334, wherein the secured end contacts the retainer 310. The adaptor 330 is formed of a plastic such as ACETAL; however, the adaptor may be formed of metals such as aluminum. As shown in FIG. 2, the adaptor 330 includes a central recess 333 which extends from the coupling end 332 to proximal to the secured end 334. The circumference of the recess 333 is defined by a diaphragm shoulder 336. The bottom of the recess 333 is defined by an inwardly projecting skirt 338 substantially coplanar with the secured end 334 of the adaptor 330. The skirt 338 includes a central aperture 339 concentric with the axis A. The central aperture 339 is sized to slidably receive the shaft 300. The skirt 338 also includes three apertures 341, 343 and (not shown) 345 equally spaced about a circumference concentric with the central aperture 339. The three apertures 341, 343, 345 in the skirt 338 are spaced so as to cooperatively align with the inner apertures 315, 317, 319 of the planar member 312 of the retainer 310. As shown in FIG. 3, the adaptor 330 is secured to the retainer 310 by fasteners 340 passed through the adaptor 330 into the retainer 310.

The coupling end 332 of the adaptor includes a circumferential contact face 348 proximal to the diaphragm shoulder 336. The outer perimeter of the contact face 348 includes an upwardly extending rim 350. The contact face 348 includes three arcuate clutches 352, 356, 360, each having a unique length. Preferably, the clutches 352, 356, 360 are spaced to define the three unique receiving areas 353, 357, 361, respectively, on the contact face 348; that is, the clutches are not 120° from each other. Each clutch 352, 356, 360 includes a horizontal flange 354, 358, 362, respectively, parallelly spaced from the contact face 348 and affixed to the rim 350, and a perpendicular stop 355, 359 (not shown), 363 (not shown), respectively, which extends from the contact face 348 to an end of the flange. The flanges 354, 358, 362 extend radially inward from the rim 350 to overlay the contact face 348. Preferably, each flange 354, 358, 362 defines a decreasing distance between the contact face 348 and the flange, as the flange extends from the open end to the stop 355, 359, 363.

As shown in FIGS. 2 and 3, the adaptor 330 includes a pneumatic conduit 366 extending from the contact face 348 to a radial port 368. The radial port 368 includes a fitting 370 which sealably connects to a line for monitoring the patient pressure.

Referring to FIG. 3, the poppet 380 is affixed to the shaft 300 within the central recess 333 of the adaptor 330. The poppet 380 includes a substantially circular contact face 382 perpendicular to the axis A. A depending cup 384 sized to receive the end of the shaft 300 extends from the contact face 382. The interior of the cup 384 includes an outwardly extending annular groove 385 sized to partially receive the O-ring 304. The interior of the cup is sized to receive the shaft 300 and the O-ring 304 to form a snap fit which retains the poppet 380 relative to the shaft. Although the face 382 of the poppet 380 may include a plurality of bumps 386 which provide the contact area between the diaphragm 390 and the poppet 380, bumps 398 are preferably formed on the corresponding portion of the diaphragm 390, as discussed infra. The bumps 386, 398 are approximately 0.015 inches high and form a hemispherical projections.

As shown in FIGS. 2 and 3, the diaphragm 390 is disposed on the diaphragm shoulder 336 of the adaptor 330. The diaphragm 390 is formed of a resilient flexible material such as silicone rubber. Preferably, the diaphragm 390 includes a relatively thick peripheral flange 392 connected to a relatively thick inner seating portion 396 by a thinner resilient flex portion 394. In the preferred embodiment, the thickness of the peripheral flange 392 is such that as the flange 392 engages the diaphragm shoulder 336, the top of the flange 392 and the contact face 348 of the adaptor 330 are substantially coplanar. Preferably, the flex portion 394 forms an arcuate U-shape to connect the peripheral flange 392 to the inner seating portion 396. Alternatively, the flex portion 394 may define an S-shaped configuration which connects the flange 392 to the seating portion 396. The flex portion 394 is configured to urge the seating portion 396 upward; that is, provide a bias against any downward motion of the seating portion 396. The seating portion 396 and the peripheral flange 392 are substantially coplanar, while the flex portion 394 may extend above or below the plane of the seating portion and the flange.

As shown in FIG. 3, the side of the seating portion 396 exposed to the poppet includes a plurality of raised bumps 398. Preferably, the bumps 398 extend from the surface of the diaphragm 390 and extend a height of approximately 0.015 inches. As discussed infra, the bumps 398 provide for the ready separation of the poppet 380 and the diaphragm 390.

Valve Body

As shown in FIGS. 2 and 3, the valve body 400 includes an inlet port 402, an outlet port 408, a fixed valve seat 406 and a pressure sense port 404, wherein the fixed valve seat 406 is disposed between the outlet port 408 and the inlet port 402, and the pressure sense port 404 is disposed between the fixed valve seat 406 and the inlet port 402. The valve body 400 includes a base 410 such that the valve seat 406 is coplanar with the base 410. The valve body 400 is formed of a plastic which is inert with respect to any element of the respiratory gases. A preferred material is polysulphone. Although the valve body 400 is described as a separate structure from the housing 100, the valve body may be formed integrally with the housing.

Referring to FIGS. 2 and 3, the inlet port 402 of the valve body is fluidly connected to a substantially cylindrical inner chamber 403. The chamber 403 terminates at the valve seat 406 conterminously with the base 410. Preferably, the valve seat 406 is a circumferential seat formed of a 0.01 inch radii. The use of a 0.01 inch radii at the valve seat 406, rather than a substantially knife edge, prevents the diaphragm 390 from being cut or degraded by repeated by contacts with the valve seat 406.

As shown in FIGS. 1-3, a substantially concentric outlet pathway 407 surrounds the inner chamber 403. The outlet pathway 407 begins with a circular outlet seat 405 having a circumference substantially equal to the peripheral flange 392 of the diaphragm 390. The outlet seat 405 is coplanar with the valve seat 406. The cylindrical portion of the outlet pathway 407 extends away from the base 410 and is intersected by the outlet port 408.

Referring to FIG. 2, the base 410 of the valve body 400 includes three radially extending tabs 412 (not shown), 414, 420 corresponding in size to the unique arcuate lengths defined by the clutches 352, 356, 360 of the adaptor 330. Therefore, the valve body 400 can only be operably engaged with the adaptor 330 in a single orientation. The tabs 412, 416, 420 are substantially planar and extend substantially coplanar with the outlet seat 405 and the valve seat 406.

To operably engage the valve body 400 to the adaptor 330, the diaphragm 390 is placed in the adaptor 330 so that the peripheral flange 392 of the diaphragm 390 seats on the diaphragm shoulder 336. The top of the peripheral flange 392 and the contact face 348 are substantially coplanar. The valve body 400 is then disposed so that the tabs 412, 416, 420 are within the corresponding receiving areas 353, 357, 361 of the contact face 348. The valve seat 406 thereby contacts the seating portion 396 of the diaphragm 390, and the outlet seat 405 contacts the peripheral flange 392 of the diaphragm 390 as it is retained on the diaphragm shoulder 336. After the tabs 412, 416, 420 are received on the contact face 314 within the respective receiving area, the valve body 400 is rotated relative to the adaptor 330, thereby disposing each of the tabs 412, 414, 420 within the corresponding clutch 352, 356, 360. As the tabs 412, 416, 420 are rotated into the corresponding clutches 352, 356, 360, the incline portion of the clutch urges the tab, and hence the valve seat 406 and outlet seat 405, against the diaphragm 390. The peripheral flange 392 of the diaphragm 390 and the outlet seat 405 thereby form a sealed relation. As the tabs 412, 414, 420 contact the stops 355, 359, 363 of the clutches 352, 356, 360, the valve body 400 is operably engaged to the adaptor 330, and the pressure sense port 404 of the valve body 400 aligns with the pneumatic conduit 366 of the adaptor 330 so that the radial port 368 is in fluid communication with the inner chamber 403 of the valve body 400.

As the exhalation valve 10 is operably assembled, the underside of the poppet 390 is exposed to atmospheric pressure. Referring to FIG. 3, the cavity 130 is exposed to atmospheric pressure through the input port 190. As the passage of the shaft 300 through the aperture 313 of retainer 310 is not a fluid tight relation, the atmospheric pressure is exposed to the central recess 333 of the adaptor 330 and hence, to the underside of the poppet 390. The exposure of the underside of the poppet, the flex portion 394 and the underside of the seating portion 396 to atmospheric pressure provides that upon the creation of a lower pressure in the inner chamber 403, the upper side of the seating portion 396 will be forced against the valve seat 406 so as to prevent the passage of air from the outlet port 408 to the inlet port 402.

Preferably, the flex portion 394 of the diaphragm 390 is configured such that upon operable assembly of the valve 10, the nominal bias of the seating portion 396 against the valve seat 406 such that a pressure in the inner chamber 403, which is approximately 0.0214 to 0.0286 psi above the atmospheric pressure, will cause the seating portion 396 to separate from the valve seat 406. The diameter of the valve seat 406 is determined by design factors, including the desired response time of the valve, the sensitivity of the diaphragm and desired axial displacement of the poppet. In a preferred embodiment, the total axial displacement of the poppet 380 relative to the valve seat 406 is approximately 0.002 inches. The diameter of the valve seat 406 is approximately 0.56 inches.

Operation of the Ventilator Exhalation Valve

During inspiration of gases, the linear actuator forces the poppet 380, hence diaphragm 390, against the fixed valve seat 406. The force of the linear actuator 450 acting on the poppet 380 provides that substantially no leakage of gases occurs through the valve 10. The forcing of the diaphragm 390 by the linear actuator 450 against the valve seat 406 also provides for the maintenance of a positive pressure within the patient.

However, for spontaneous inspirations when the linear actuator is unenergized, the diaphragm 390 is nominally biased so as to urge the seating portion 396 against the valve seat 406. As the poppet side of the diaphragm 390 is exposed to atmospheric pressure, a reduced pressure in the lungs during inspiration will not draw air from the outlet port 408 through the exhalation valve 10. The diaphragm 390 thereby acts as a check valve to prevent flow through the valve 10 in the reverse direction and ensure inspiration of fresh gases.

Upon termination of the inhalation phase and initiation of the exhalation phase, the control mechanism directs a current to the coil 480 which draws the poppet 380 way from the valve seat 406 and the patient pressure from the inlet port 402 becomes sufficient to overcome the nominal bias of the diaphragm 390 against the valve seat 406. The seating portion 396 of the diaphragm 390 then separates from the valve seat 406 and flow passes from the inlet port 402, between the valve seat 406 and the diaphragm 390, to the outlet port 408. As the flow causes the diaphragm 390 to separate from the valve seat 406, the underside of the seating portion 396 contacts the poppet 380. The poppet 380, and hence shaft 300, including the moveable coil 480 and the ferromagnetic portion 307, are correspondingly displaced. As the ferromagnetic portion 307 is displaced relative to the stationary coil 230 of the feedback assembly 200, the feedback signal is generated in the stationary coil 230. This feedback signal is proportional to the velocity and the direction of motion of the shaft 300, poppet 380 and diaphragm 390 relative to the valve seat 406. The feedback signal is transferred through the signal pathway 234 to the control mechanism. The control mechanism employs the velocity feedback signal to stabilize the valve motion and eliminate the undesired oscillations inherent in these types of valves. In addition, the generation of the velocity feedback signal induces a dampening to the axial motion of the shaft 300 and poppet 380, reducing the sensitivity of the valve to flow turbulence.

The actuation of the linear actuator 450, and hence axial displacement of the poppet 380 and diaphragm 390, is controlled by a current from the control mechanism. The current passes through the flexible lead 490 to the moveable coil 480. The presence of a current in the moveable coil 480 creates an electromagnetic force between the permanent magnet 460 and the coil 480. This force causes the moveable coil 480, drum 482, and hence shaft 300 and poppet 380 to be axially displaced. This axial movement of the poppet 380 provides for regulation of the poppet 380 relative to the valve seat 406 and the diaphragm 406. As the poppet 380 may be directed towards the valve seat 406, the diaphragm 390, as disposed therebetween, also approaches the valve seat 406, thereby reducing the flow from the inlet port 402 to the outlet port 408.

As the exhalation phase ends, current to the moveable coil 480 is applied, as required, to seat the diaphragm 390 against the fixed valve seat 406. The bumps 398 on the surface of the diaphragm 390 provide for a non-binding contact between the diaphragm 390 and the poppet 380 so that the diaphragm 390 readily separates from the poppet 380 under both moist and dry conditions.

When the proximal pressure is to be regulated, the pressure from the sensing port 404, hence pressure proximate to the inlet port 402, is monitored. This pressure is fed to an external pressure transducer (not shown) which converts the signal to an electrical analog. The external closed loop control mechanism continuously compares this pressure to a set reference and accordingly adjusts the current to the moveable coil 480. For example, if the proximal pressure were low with respect to the reference pressure, the control mechanism would increase the current to the moveable coil 480, which would move the poppet 380, and diaphragm 390 towards the valve seat 406, thereby decreasing the flow area through the valve 10. The reduced flow area would in turn raise the pressure in the lungs. As the diaphragm 390 is forced against the valve seat 406 by the poppet 380, the proximal pressure is regulated. The proximity of the pressure sense port 404 and the responsiveness of the linear actuator 450 permits the substantially instantaneous and continuous control of the proximal pressure.

Although the present invention has been described in terms of particular embodiments, it is not limited to these embodiments. Alternative embodiments and modifications which would still be encompassed by the invention may be made by those skilled in the art, particularly in light of the foregoing technique. Alternative embodiments, modifications, or equivalents may be included within the spirit and scope of the invention as defined by the claims.

We claim:

1. A ventilator exhalation valve for permitting the passage of fluid flow from the lungs of a patient to the atmosphere while precluding the passage of fluid from the atmosphere to the lungs, the valve having a forward fluid flow direction in which fluid flow through the valve is permitted and a reverse fluid flow direction in which fluid flow through the valve is prevented, the valve comprising:

(a) a housing assembly having an inlet port exposed to the lungs, an outlet port exposed to the atmosphere and a valve seat wherein the valve seat is intermediate of and fluidly connected to the inlet port and the outlet port;

(b) a diaphragm disposed proximal to the valve seat so as to selectively prevent flow through the valve, the diaphragm being displaced from the valve seat by fluid flow through the valve in the forward direction;

(c) a poppet disposed proximal to the diaphragm so that the poppet selectively contacts the diaphragm;

(d) a linear actuator mechanically connected to the poppet for selectively positioning the poppet relative to the valve seat; and (e) a feedback assembly in communication with the poppet, providing a feedback signal corresponding to the velocity of the poppet relative to the valve seat for controlling the linear actuator.

2. The ventilator exhalation valve of claim 1 further comprising: a pressure sense port in the housing assembly, the pressure sense port disposed between the valve seat and the inlet port, and fluidly connected to the inlet port.

3. The ventilator exhalation valve of claim 1 further comprising: a suspension assembly for providing substantially frictionless motion of the poppet relative to the valve seat, the suspension system including at least one spring flexure connecting the poppet relative to the housing assembly so as to permit axial displacement of the poppet relative to the valve seat while substantially precluding radial displacement of the poppet relative to the valve seat.

4. A ventilator exhalation valve, comprising:
  (a) a housing assembly having an inlet port, an outlet port, a pressure sense port and a valve seat, wherein the valve seat is disposed between the inlet port and the outlet port, and the pressure sense port is disposed between the valve seat and the inlet port;
  (b) a resilient diaphragm disposed proximal to the valve seat such that upon a fluid flow from the inlet port to the outlet port the diaphragm is separated from the valve seat;
  (c) a poppet disposed proximal to the diaphragm so that the diaphragm is between the poppet and the valve seat, wherein the poppet selectively contacts the diaphragm so as to permit independent motion of the poppet relative to the diaphragm;
  (d) a suspension assembly for retaining the poppet relative to the housing, the suspension system including at least one substantially planar spring flexure connecting the poppet and the housing; and
  (e) a feedback assembly in communication with the poppet for providing a feedback signal corresponding to the velocity of the poppet relative to the valve seat, the feedback assembly including a passive coil and a ferromagnetic element moveable relative to each other.

5. A ventilator exhalation valve, comprising:
  (a) a housing assembly including an inlet port, an outlet port and a valve seat fluidly connected to and intermediate of the ports;
  (b) a diaphragm disposed proximal to the valve seat and biased against the valve seat for selectively preventing fluid flow between the inlet port and the outlet port, and for preventing fluid flow from the outlet port to the inlet port;
  (c) a linear actuator for selectively controlling the position of the diaphragm relative to the valve seat so as to regulate the amount of fluid flow between the inlet port and the outlet port; and
  (d) a feedback assembly connected to the linear actuator for providing a feedback signal corresponding to the velocity of the diaphragm relative to the valve seat, the feedback assembly including a passive coil and a ferromagnetic element moveable relative to each other.

6. A ventilator exhalation valve, comprising:
  (a) a housing assembly including an inlet port, an outlet port and a valve seat, wherein the valve seat is disposed intermediate of and fluidly connected to the inlet port and the outlet port;
  (b) a diaphragm disposed proximal to the valve seat for selectively providing fluid flow between the inlet port and the outlet port;
  (c) a linear actuator having a moveable member for physically contacting the diaphragm so as to regulate the fluid flow between the inlet port and the outlet port; and
  (d) a suspension assembly for retaining the moveable member of the linear actuator relative to the housing wherein the suspension assembly includes a spring flexure attached to the moveable member for permitting axial motion of the moveable member relative to the housing while preventing radial motion of the moveable member relative to the housing.

* * * * *